United States Patent
Yasuoka et al.

(10) Patent No.: US 7,282,610 B2
(45) Date of Patent: Oct. 16, 2007

(54) METHOD OF PRODUCING AROMATIC AMINE COMPOUND HAVING ALKYLTHIO GROUP

(75) Inventors: Hiroshi Yasuoka, Odawara (JP); Hideto Mori, Odawara (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 10/995,315

(22) Filed: Nov. 24, 2004

(65) Prior Publication Data

US 2005/0283024 A1    Dec. 22, 2005

(30) Foreign Application Priority Data

Nov. 28, 2003    (JP)    ............... 2003-399986

(51) Int. Cl.
*C07C 209/34* (2006.01)
*C07C 209/36* (2006.01)
(52) U.S. Cl. .............. 564/416; 564/417; 564/418
(58) Field of Classification Search .................. None
See application file for complete search history.

(56) References Cited

U.S. PATENT DOCUMENTS 3,386,991 A * 6/1968 Gerber .............. 534/600

5,977,413 A * 11/1999 Tomaru et al. ............. 564/423

FOREIGN PATENT DOCUMENTS

| EP | 0 595 230 A1 | 5/1994 |
|---|---|---|
| HU | 54 978 A2 | 4/1991 |
| JP | 51-125027 A | 11/1976 |
| JP | 6-271175 A | 10/1993 |
| JP | 2002-193899 A | 7/2002 |

OTHER PUBLICATIONS

Nihon Kagakukaishi, The Journal of Japanese Chemical Society, pp. 858-863, 1978.
Toshiyuki Miyata et al.; Synthesis, pp. 834-835, 1978.
Database Beilstein Accession Nos. 2486547 and 1067782 (1990).

* cited by examiner

*Primary Examiner*—Brian Davis
(74) *Attorney, Agent, or Firm*—Birch, Stewart, Kolasch & Birch, LLP

(57) ABSTRACT

A method of producing an aromatic amine compound, that includes reducing an aromatic nitro compound that has an aromatic ring having an alkylthio group as a substituent, to obtain a corresponding aromatic amine compound, wherein the aromatic nitro compound is reduced using a hydrazine compound in the presence of an iron compound and an activated carbon.

16 Claims, No Drawings

METHOD OF PRODUCING AROMATIC AMINE COMPOUND HAVING ALKYLTHIO GROUP

FIELD OF THE INVENTION

The present invention relates to a method of producing an aromatic amine compound having an alkylthio group. Particularly, the present invention relates to a method of producing an aromatic amine compound having an alkylthio group, that is useful as a synthetic intermediate for dyes, color marking materials, medical supplies, agrochemicals, electronic materials, or silver halide photographic light-sensitive materials.

BACKGROUND OF THE INVENTION

Reduction of a nitro group of compounds is one of the most important reactions in organic synthesis. Various reduction methods are known, including catalytic reduction using hydrogen in the presence of a catalyst; reduction using a hydrazine compound, an olefin compound, such as cyclohexene, or formic acid, in the presence of a catalyst; reduction using an iron carbonyl compound; reduction using a hydrogenated aluminum compound, such as hydrogenated lithium aluminum; reduction using a hydrogenated boron compound, such as hydrogenated boron sodium, or a combination of a hydrogenated boron compound and a metal compound (e.g. nickel chloride, and copper acetate); reduction using zinc or tin in the presence of hydrochloric acid; reduction using an activated iron powder; reduction using a sulfide, and reduction using sodium hydrosulfite (for example, S. R. Sandler, W. Karo, ORGANIC FUNCTIONAL GROUP PREPARATIONS, Second Edition, Volume I, Academic Press, Inc, 1983, pp. 405-411; and L. C. Larock, COMPREHENSIVE ORGANIC TRANSFORMATIONS, A Guide to Functional Group Transformations, VCH Publishers, Inc, 1989, pp. 411-415).

In recent years, influences to environment of chemical production processes have drawn much attention. As such, there is a demand for a clean chemical reaction that is run under mild reaction conditions; that is reduced in wastes, and that needs least-possible amounts of harmful reaction agents.

For the problems stated above, reduction reactions of a nitro group of compounds have problems enumerated below.

(1) Reduction using an iron carbonyl compound: The reaction agent is toxic and expensive.

(2) Reduction using a hydrogenated aluminum compound: The reaction agent is expensive and is unstable against moisture, which can be dangerous.

(3) Reduction using a hydrogenated boron compound: The reaction agent is expensive and is unstable against moisture, which can be dangerous.

(4) Reduction using zinc or tin in the presence of hydrochloric acid: Disposal of an acidic effluent containing metals, is difficult.

(5) Reduction using an activated iron powder: Much iron waste is generated, and disposal of it is difficult.

(6) Reduction using a sulfide: The sulfide has an unacceptable odor, and disposal of effluents containing the sulfide, is difficult.

(7) Reduction using sodium hydrosulfite: Treatment of waste fluids is troublesome, and the reaction is difficult in an organic solvent system.

(8) As to the conditions of these reactions, an excess amount of reaction agent is used to complete the reaction, in almost all cases, which not only increases cost but also causes complicated work, including disposal of wastes in after-treatment following the reaction.

As a method to solve such problems, use of a catalyst is practical. Catalytic reduction using hydrogen, and hydrazine reduction, in the presence of a catalyst, such as palladium, platinum, or nickel, are well known. These methods, however, cannot be applied to almost all cases of using a substrate in which a low-valence sulfur functional group, such as a sulfide, coexists in its molecule. Further, even contamination by a small amount of a low-valence sulfur compound, in the substrate, can make reduction difficult, in many cases.

In the meantime, as a method to reduce a nitro group to an amino group of compounds, in a reduction method using hydrazine, there are known a method using iron oxides together (for example, Nihon Kagakukaishi (the Journal of Japanese Chemical Society), pp. 858-863 (1978)), and a method using ferric chloride and activated carbon together (for example, JP-A-51-125027 ("JP-A" means unexamined published Japanese patent application), JP-A-5-271175, JP-A-6-135905, JP-A-2002-193899, and Synthesis, pp. 834-835 (1978)). However, these methods make no reference to the reduction of a nitro group of a compound having a low-valence sulfur functional group, such as a sulfide, in its molecule.

SUMMARY OF THE INVENTION

The present invention is a method of producing an aromatic amine compound, which comprises reducing an aromatic nitro compound that has an aromatic ring substituted by an alkylthio group, to obtain an aromatic amine compound that has an aromatic ring substituted by an alkylthio group, wherein the aromatic nitro compound is reduced using a hydrazine compound in the presence of an iron compound and an activated carbon.

Other and further features and advantages of the invention will appear more fully from the following description.

DETAILED DESCRIPTION OF THE INVENTION

The inventors of the present invention have found that a reduction reaction proceeds, in a method of reducing a nitro compound, in which a low-valence sulfur functional group, such as an alkylthio group, coexists in its molecule, or of reducing a nitro compound containing a dialkyl sulfide and/or a dialkyl disulfide as impurities, in the presence of activated iron powder. As mentioned above, however, much iron waste is generated; the filterability of the waste is poor; the filtered iron waste produces heat, which can be dangerous; and also, the washing of a kettle after the reaction is finished is troublesome. These methods are therefore quite unfit for mass production, for the above reasons.

As a result of intensive studies, the present inventors have found that the above-mentioned problems can be solved by employing the following measures.

According to the present invention, there are provided:

(1) A method of producing an aromatic amine compound, comprising reducing an aromatic nitro compound, which comprises an aromatic ring that has an alkylthio group as a substituent, to obtain a corresponding aromatic amine compound, wherein the aromatic nitro compound is reduced using a hydrazine compound in the presence of an iron compound and an activated carbon.

(2) The production method according to the above (1), wherein the aromatic ring of the aromatic nitro compound further has a tertiary alkyl group as a substituent.

(3) The production method according to the above (1) or (2), wherein said iron compound is a ferrous or ferric compound.

(4) The production method according to the above (3), wherein said iron compound is a ferric compound.

(5) The production method according to the above (4), wherein said ferric compound is at least one compound selected from hydrated iron (III) oxide, a ferric halide, a ferric sulfate, and a ferric nitrate.

(6) The production method according to any one of the above (1) to (5), wherein the aromatic nitro compound is a compound represented by the following formula (II), and the corresponding aromatic amine compound is a compound represented by the following formula (I):

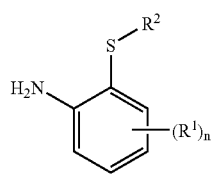

formula (I)

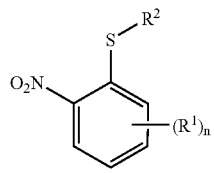

formula (II)

wherein in formulae (I) and (II), $R^1$ represents a substituent; n denotes an integer from 0 to 4; when n is 2 or more, plural $R^1$s may be the same or different and may combine each other to form a ring; and $R^2$ represents an alkyl group.

(7) The production method according to any one of the above (1) to (5), wherein the aromatic nitro compound is a compound represented by the following formula (IV), and the corresponding aromatic amine compound is a compound represented by the following formula (III):

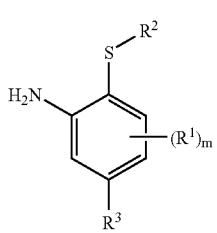

formula (III)

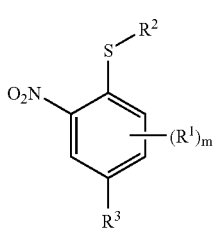

formula (IV)

wherein, in formulae (III) and (IV), $R^1$ represents a substituent, m denotes an integer from 0 to 3; when m is 2 or more, plural $R^1$s may be the same or different and may combine each other to form a ring; $R^2$ represents an alkyl group; and $R^3$ represents a tertiary alkyl group.

The present invention will be explained in detail below.

First, the aromatic nitro compound having an alkylthio group on its aromatic ring, for use in the present invention, will be explained.

The aromatic nitro compound for use in the present invention is a compound that has an aromatic ring having a nitro group and an alkylthio group. The aromatic ring may have a substituent besides the nitro group and alkylthio group. Although the details of such substituent will be explained later, the substituent other than the nitro group and alkylthio group is one of those having preferably at least one alkyl group and more preferably at least one tertiary alkyl group. Also, examples of the aromatic ring include a benzene ring, condensed polycyclic hydrocarbon rings, such as a naphthalene ring, and phenanthrene ring; and heteroaromatic rings, such as a pyridine ring. The aromatic ring is preferably a benzene ring or a condensed polycyclic hydrocarbon ring, and more preferably a benzene ring.

Preferable examples of the aromatic nitro compound may be represented by the following formula (B).

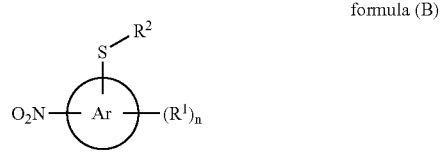

formula (B)

In formula (B), Ar represents an aromatic ring. $R^1$ represents a substituent. n denotes an integer from 0 to 4. When n is 2 or more, plural $R^1$s may be the same or different and may combine each other to form a ring. $R^2$ represents an alkyl group.

Specific examples of Ar include a benzene ring and a naphthalene ring, and a benzene ring is preferred.

Examples of $R^1$ include a halogen atom, an alkyl group, a cycloalkyl group, an alkenyl group, a cycloalkenyl group, an aryl group, a heterocyclic group, a hydroxyl group, an alkoxy group, an aryloxy group, an amino group (including an alkylamino group and an anilino group), an acylamino group, a sulfamoylamino group, a mercapto group, an alkylthio group, an arylthio group, a sulfamoyl group, a carbamoyl group, and an alkyl- or aryl-sulfonyl group.

Preferable examples of $R^1$ include alkyl groups (straight-chain or branched, substituted or unsubstituted alkyl groups, preferably alkyl groups having 1 to 30 carbon atoms, for example, methyl, ethyl, n-propyl, isopropyl, t-butyl, t-amyl (1,1-dimethylpropyl), t-octyl(1,1,3,3-tetramethylbutyl), n-octyl, eicosyl, 2-ethylhexyl, and 3-(2,4-di-t-amylphenoxy) propyl), aryl groups (preferably, substituted or unsubstituted aryl groups, preferably aryl groups having 6 to 30 carbon atoms, for example, phenyl, 4-octyloxyphenyl, 4-decylphenyl, 2,4-dichlorophenyl, and naphthyl), halogen atoms (e.g., chloro and bromo), alkoxy groups (substituted or unsubstituted alkoxy groups, preferably alkoxy groups having 1 to 30 carbon atoms, for example, methoxy, butoxy, 2-ethylhexyloxy group, and octadecyl group), and aryloxy groups (substituted or unsubstituted aryloxy groups, preferably aryloxy groups having 6 to 30 carbon atoms, for example, phenoxy, 4-methylphenoxy, 4-methoxyphenoxy, 2,4-dichlorophenoxy, and 2-methyl-4-myristoylaminophenoxy).

n is an integer from 0 to 4, preferably 1 or 0, and more preferably 1.

$R^2$ is preferably a straight- or branched-chain, substituted or unsubstituted alkyl group. $R^2$ is preferably an alkyl group having 1 to 30 carbon atoms, e.g., methyl, ethyl, n-propyl, isopropyl, t-butyl, n-octyl, eicosyl, 2-chloroethyl, 2-cyanoethyl, 2-ethylhexyl, and 3-(2,4-di-t-amylphenoxy)propyl). $R^2$ is preferably an alkyl group having no substituent except for an alkyl group(s), $R^2$ is more preferably an alkyl group having, as a substituent(s), another alkyl group(s) at the β-position (i.e. a branched alkyl group which is branched at least at the β-position), and $R^2$ is most preferably 2-ethylhexyl.

Among the compounds represented by formula (B), compounds having an alkyl group as one of $R^1$s are preferable.

$R^1$ is more preferably a tertiary alkyl group; and the aromatic nitro compound can be represented by the following formula (B)'.

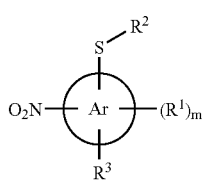

formula (B)'

In formula (B)', Ar, $R^1$, and $R^2$ have the same meanings as those in formula (B) and their respective preferable ranges are also the same as those in formula (B). m denotes an integer of 0 to 3. $R^3$ represents a tertiary alkyl group.

m is preferably 0.

$R^3$ is a substituted or unsubstituted tertiary alkyl group. $R^3$ is preferably a tertiary alkyl group having 4 to 30 carbon atoms; e.g., t-butyl, t-amyl(1,1-dimethylpropyl), t-octyl(1,1,3,3-tetramethylbutyl), and 1,1-dimethylbenzoyl). $R^3$ is preferably t-butyl group, t-amyl group, or t-octyl group, more preferably t-butyl or t-octyl group, and most preferably t-butyl group.

On the other hand, when focused on Ar, preferable examples of the compound represented by formula (B) can be expressed by the following formula (II).

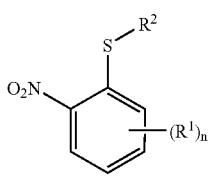

formula (II)

In formula (II), $R^1$, $R^2$, and n have the same meanings as those in formula (B) and their respective preferable ranges are also the same as those in formula (B).

The compound represented by formula (II) is preferably a compound represented by formula (IV).

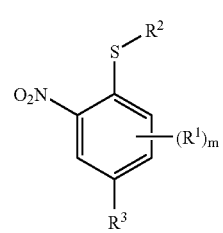

formula (IV)

In formula (IV), $R^1$, $R^2$, $R^3$, and m have the same meanings as those in formula (B)' and the respective preferable ranges are also the same as those in formula (B)'.

Next, the aromatic amine compound having an alkylthio group on its aromatic ring, for use in the present invention, will be explained in detail.

The aromatic amine compound that has an aromatic ring having an alkylthio group is a compound obtained by reducing a nitro group to an amino group in the corresponding aromatic nitro compound that has an aromatic ring having an alkylthio group. Therefore, preferable compounds are those represented by the formulas and each group, which are obtained by replacing the nitro group with an amino group in the formulas and each group described for the aforementioned aromatic nitro compounds.

Specifically, the aromatic amine compounds are compounds represented by the following formulae (A), (A)', (I), and (III), wherein each group has the same meaning as that in the corresponding formulae (B), (B)', (II), and (IV), respectively, and the preferable range thereof is also the same.

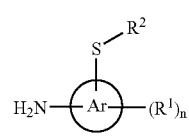

formula (A)

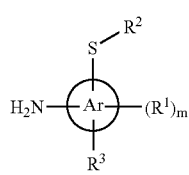

formula (A)'

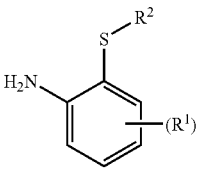

formula (I)

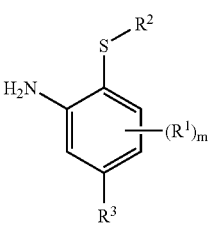

formula (III)

Specific examples of the aromatic nitro compounds for use in the present invention are shown below, but the present invention is not limited to these.
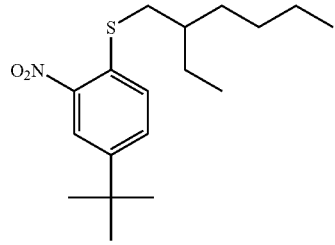
(1)
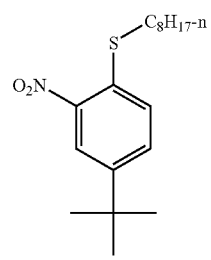
(2)
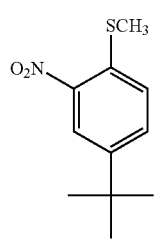
(3)
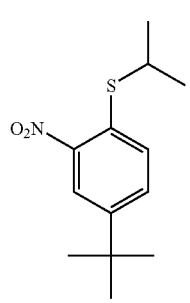
(4)
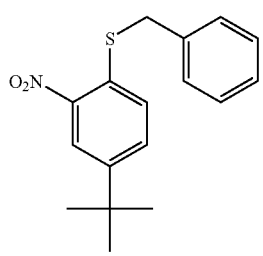
(5)
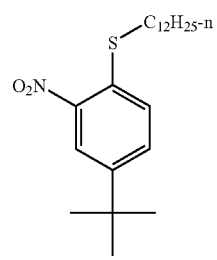
(6)
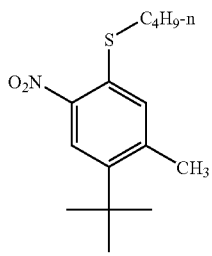
(7)
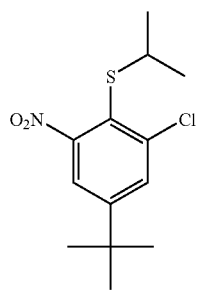
(8)
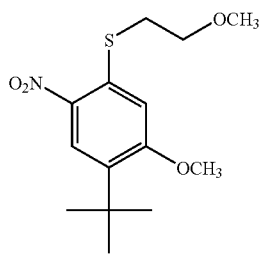
(9)
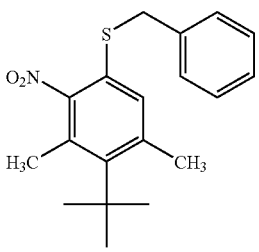
(10)
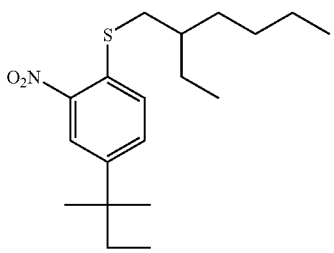
(11)

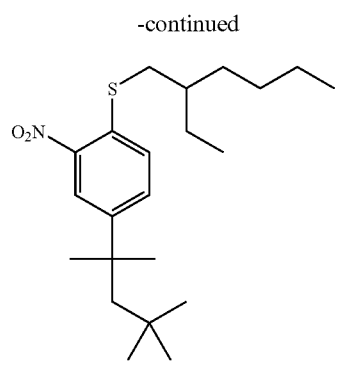
(12)
Specific examples of the aromatic amine compounds, which can be obtained by the method of the present invention, are shown below, but the present invention is not limited to these.
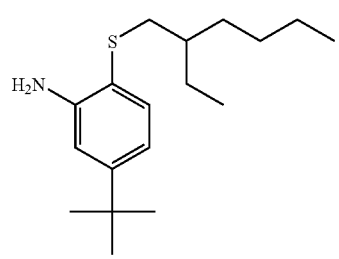
(21)
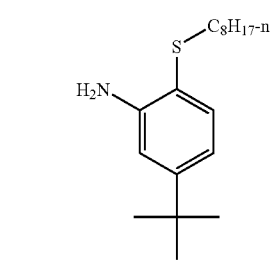
(22)
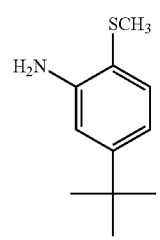
(23)
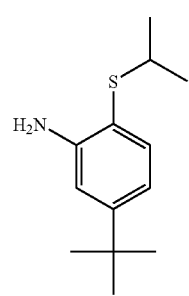
(24)
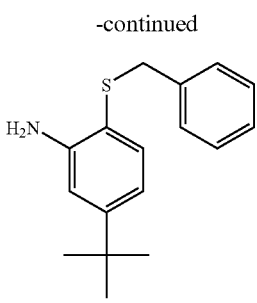
(25)
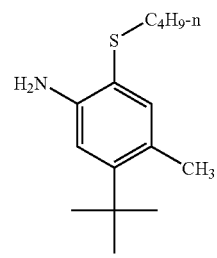
(26)
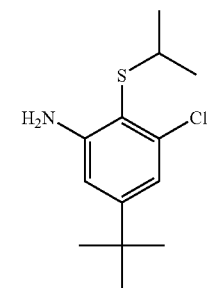
(27)
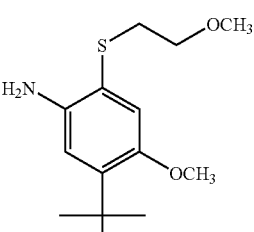
(28)
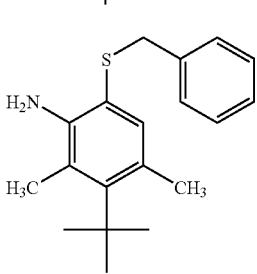
(29)
(30)

-continued

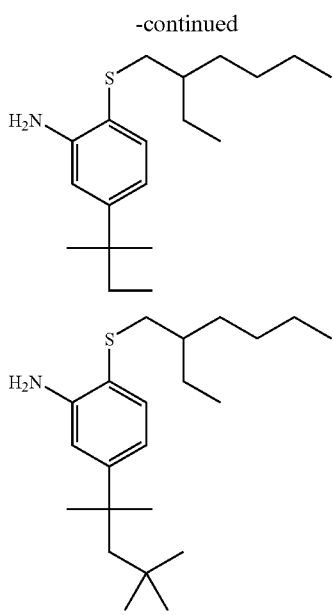

(31)

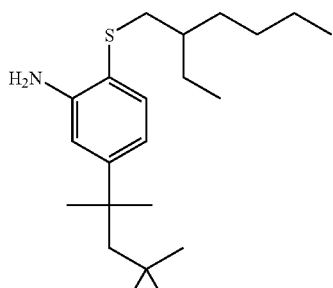

(32)

Next, production conditions, including a reducing agent, in the production method of the present invention will be explained in detail.

First, the aromatic nitro compound that has an aromatic ring having an alkylthio group may be produced with ease by a nucleophilic substitution reaction, by an alkyl mercaptan compound, of an aromatic nitro compound that has an aromatic ring having a halogen atom as a substituent (Journal of Medicinal Chemistry, vol. 46, page 169 (2003) and Journal of Medicinal Chemistry, vol. 23, page 717 (1980)) and by a S-alkylation reaction of an aromatic nitro compound having a mercapto group on its aromatic ring (Zhumal Organicheskoi Khimii, vol. 20, page 1045 (1984)). Also, as a modification of the former method, $S^{2-}$ may be added to a system, in which an alkyl halide and an aromatic nitro compound that has an aromatic ring having a halogen atom as a substituent, coexist, to produce the target compound. The aromatic nitro compound having an alkylthio group on its aromatic ring, produced in such a method, may be subjected to the production method of the present invention, after it is subjected to isolation and purification. Alternatively, the aromatic nitro compound thus obtained can be used, without isolating it from the reaction substance after reaction, successively, in the reduction reaction according to the present invention; and as such the present reduction method is industrially advantageous. Particularly, the present reduction method is advantageous because the aromatic amine compound can be produced, without deteriorating its yield, from the aromatic nitro compound, containing starting material, wherein the purity of the aromatic nitro compound is 90% or less, and even it is 85% or less (the lower limit is preferably 50%).

The reduction in the present invention is characterized by the use of a hydrazine compound as a reducing agent, in the presence of an iron compound and an activated carbon.

The hydrazine compound for use in the reduction according to the present invention is generally $NH_2NH_2$, including its hydrate or salt, and the hydrazine compound is preferably hydrazine monohydrate or its aqueous solution. Among these, an aqueous 80% solution of hydrazine monohydrate is most preferable from the viewpoint of safety and handling. The amount of the hydrazine compound to be used for the reduction reaction in the present invention is generally in a range from 1.5 to 10.0 mol, preferably 1.5 to 5.0 mol, and more preferably 1.8 to 3.0 mol, per mol of the aromatic nitro compound, which is the starting material.

The iron compound for use in the present invention will be explained.

In the reduction of the aromatic nitro compound having an alkylthio group, according to the present invention, when the metal catalyst to be used in combination with the hydrazine compound is palladium, platinum, or a Raney nickel catalyst, the reduction reaction does not proceed or is greatly suppressed. This is assumed that these metal catalysts are poisoned by the low-valence sulfur compound. It is assumed that because soft metals have high affinity to soft low-valence sulfur compounds, the interaction between these metals and hydrogen is scarcely caused, as such hydrogen occlusion is accomplished ineffectively.

The iron compound for use in the present invention is preferably a ferrous or ferric compound, and particularly preferably a ferric compound.

As the iron compound, various forms, such as a powder form, granular form, flaky form, and solution form, which are commercially available, may be used.

Examples of the iron compound for use in the present invention include iron (III) oxide, hydrated iron (III) oxides, ferric halides (may be any form of an anhydride, hydrate, and aqueous solution), ferrous halides, ferric sulfate, ferric nitrate, and ferric acetate. In the present invention, hydrated iron oxides, ferric halides, ferrous halides, and ferric nitrate are more preferable, hydrated iron oxides, ferric halides, and ferrous halides are still more preferable, and ferric chloride hexahydrate is most preferable. In the present invention, these iron compounds may be formed in the reaction system, prior to the reduction reaction, by adding a compound containing iron and a compound containing the counter molecule, in the reaction system.

In the present invention, as the iron compound, a plurality of iron compounds may be used in combination.

The amount of the iron compound in the present invention is preferably in a range from 0.005 to 50.0 mass %, based on the aromatic nitro compound, which is the raw material. An excessive amount of the iron compound does not have much influence on an improvement of yield/production rate of the target product. What is more, excessive use of the iron compound requires complicated operations to remove iron ions in a subsequent process, leading to an increase in the amount of waste; and this is a hindrance to carry out the production process on an industrial scale.

The amount of the iron compound to be used in the present invention is more preferably 0.01 to 10.0 mass %, and still more preferably 0.02 to 5.0 mass %, based on the raw material, the aromatic nitro compound.

As the activated carbon to be used in combination with the iron compound, in the reduction reaction according to the present invention, any activated carbon has an effect on accelerating the reaction. However, the type of activated carbon should be properly selected, to obtain an aromatic amine compound, with high purity and at a high yield. The activated carbon for use in the present invention is preferably a powdery activated carbon, more preferably a steam-activated carbon produced from ligneous raw material as a base by gas activation method; and still more preferably a highly developed activated carbon having a peak pore diameter in the vicinity of 20 angstroms, a high purity activated carbon being preferable. The ignition residue (fixed solid) is preferably 2.0 mass % or less, and more preferably 1.5 mass % or less. Examples of the activated carbon for use in the present invention include "Taikon" (trade name, manufactured by Futamura Chemical Co., Ltd.) and "Sirasagi A" (trade name, manufactured by Takeda Pharmaceutical Company Limited).

The amount of the activated carbon to be used in combination with the iron compound, in the reduction reaction according to the present invention, is generally in a range from 0.1 to 200 mass %, preferably 0.5 to 50 mass %, and more preferably 1 to 20 mass %, based on the raw material, the aromatic nitro compound.

As to the reaction solvent that can be used in the reduction according to the present invention, there is no particular limitation and any solvent may be used, insofar as it does not bring about any problem on process operations, such as stirring inferiors caused by a precipitation of a reaction substrate/reaction intermediate/reaction product; it does not hinder the progress of the reaction; and it does not decompose under the reaction conditions in the present invention, to adversely affect the reaction.

Examples of the reaction solvent include alcohol type solvents (e.g., methanol, ethanol, and 2-propanol), non-protonic polar solvents (e.g., amide/urea type solvents such as N,N-dimethylformamide, N-methylpyrrolidone, and N,N-dimethylimidazolidinone; and sulfone type solvents such as sulfolane), ether type solvents (e.g., 1,2-dimethoxyethane, tetrahydrofuran, and anisole), aromatic solvents (e.g., benzene, toluene, xylene, and chlorobenzene), basic solvents (e.g., pyridine), and water. These solvents may be used either singly or in combination of two or more.

As the reaction solvent, an alcohol type solvent, a non-protonic polar solvent, a basic solvent, and water are preferable; and a combination of two or three kinds selected from alcohol type solvents, aromatic type solvents (particularly, aromatic hydrocarbon type solvents), and water, are preferable. An alcohol type solvent, a non-protonic polar solvent (particularly, amide type and urea type solvents are preferable, and N-methylpyrrolidone and N,N-dimethylimidazolidinone are more preferable), water, and a combination of two or three kinds selected from alcohol type solvents, aromatic hydrocarbon type solvents, and water, are more preferable. The solvent is most preferably a single alcohol type solvent or a combination of two or three kinds selected from alcohol type solvents, water, and aromatic hydrocarbon type solvents.

The reaction temperature in the reduction operation according to the present invention, which reaction is carried out using the hydrazine compound as a reducing agent in the presence of the iron compound and the activated carbon, is usually in a range from 20 to 200° C., preferably in a range from 40 to 150° C., and more preferably in a range from 50 to 100° C. The reaction time is usually 0.5 to 20 hours, and more preferably in a range from 1 to 10 hours, though it varies depending on the reaction substrate, charge amount, and reaction temperature. An inert atmosphere is not particularly necessary; however, the reaction may be carried out in an argon or nitrogen stream.

In the reduction reaction according to the present invention, it is preferable that a mixture of the aromatic nitro compound, iron compound, activated carbon, and reaction solvent, is heated to the reaction temperature (for several minutes, specifically, preferably for 1 to 30 minutes, more preferably 3 to 20 minutes, and still more preferably 5 to 10 minutes) under stirring, and then the hydrazine compound is added (preferably added dropwise) to the mixture.

In an after-treatment of the reaction mixture after completion of the reduction reaction, the iron catalyst and the activated carbon are separated by filtration; and then the filtrate is washed with water, extracted with hydrochloric acid, and washed with water, followed by concentrating the solution, to obtain the aromatic amine compound. This solution may be further treated, according to the quality of the aromatic nitro compound as the starting material, the qualities required for the aromatic amine compound as the target product or the form of the target product (especially, one in a liquid form). Specifically, the obtained solution may be treated using a proper acid (an organic or inorganic acid, for example, benzenesulfonic acid, p-toluenesulfonic acid, naphthalenedisulfonic acid, hydrochloric acid, and sulfuric acid; organic acids are preferable and among these organic acids, benzenesulfonic acid and p-toluenesulfonic acid are preferable) in an appropriate solvent, to carry out purification by forming a salt, followed by filtration, to obtain the target product as a salt. The thus-obtained salt may be further neutralized using an alkali to free the product, and the freed product is extracted with an organic solvent. The extract is concentrated and then diluted with a proper solvent, to obtain a solution containing the target product in a proper amount.

In a typical example of a specific production method, ferric chloride hexahydrate and an activated carbon are added to a 2-propanol solution of 5-tert-butyl-2-(2-ethylhexylthio)nitrobenzene, and the mixture is refluxed under heating for 10 minutes. To this solution is added, dropwise, an aqueous 80% solution of hydrazine monohydrate. After the addition is finished, the reaction is continued under refluxing until the raw material disappears. Then, the reaction solution is cooled, and the catalyst and the activated carbon are separated by filtration. Toluene is added to the filtrate, and the toluene solution is then washed with water, washed with an acid, neutralized, washed with water, and then concentrated, to obtain 5-tert-butyl-2-(2-ethylhexylthio)aniline.

The product, the aromatic amine compound, obtained in the above manner usually has purity of a level that it can be used in subsequent steps without further purification. It is, however, possible to purify the product by adding a proper acid, in a proper solvent, to form a salt, and use the refined salt in subsequent steps.

According to the method of the present invention, it is possible to produce an aromatic amine compound having an alkylthio group, that is useful as a synthetic intermediate for dyes, medical supplies, agrochemicals, electronic materials, silver halide photographic light-sensitive materials, or the like, economically on an industrial scale, with good efficiency, at high yield and with high purity, while reducing environmental loads and reducing generation of waste as much as possible.

The method of the present invention can be economically put into practice on an industrial scale, and can produce a high-purity aromatic amine compound having an alkylthio group, at a high yield, while reducing environmental loads and decreasing the generation of waste as much as possible.

The present invention will be hereinafter explained in more detail by way of examples. However, these examples are not intended to be limiting of the invention.

EXAMPLES

Example 1

Synthesis of Exemplified Compound (21) (Ferric Chloride was Used as the Iron Compound))

In 40 ml of isopropyl alcohol, 20 g of 5-tert-butyl-2-(2-ethylhexylthio)nitrobenzene (Exemplified compound (1)) was dissolved. To this solution were added 0.1 g of ferric chloride-hexahydrate and 1.0 g of activated carbon, and the mixture was heated under refluxing for 10 minutes. To this solution, 6.31 g (100.8 mmol, 1.7 eq) of an aqueous 80% solution of hydrazine monohydrate was added dropwise, over one hour or more. After the addition was finished, the solution was subjected to after-reaction under refluxing for 4 hours, and then cooled to 40° C. The reaction solution was subjected to filtration using celite, and the filtrate was then washed with 20 ml of toluene. 50 ml of water was added to the filtrate, to conduct phase separation, and then the organic phase was washed with 40 ml of 0.45 mass % dilute hydrochloric acid aqueous solution, to carry out phase separation. 40 ml of water was further added to the solution, and the solution was neutralized by adding aqueous sodium bicarbonate, and phase separation was conducted, to obtain a toluene solution of Exemplified compound (21).

To this solution, 40 ml of toluene was added, and then 11.27 g (59.3 mmol, 1.0 eq) of p-toluenesulfonic acid monohydrate was added and dissolved under heating. Then, the solution was cooled to crystallize, thereby obtaining 24.5 g (yield: 85%) of p-toluene sulfonic acid (PTS) salt of Exemplified compound (21).

Each NMR spectrum data of the exemplified compound (21) and the PTS salt of the compound is shown below.

Exemplified Compound (21)

H-NMR (CDCl$_3$): δ(TMS)=7.29 (1H, d, J=8.1 Hz, 6-H), 6.74 (1H, dd, J=2.1, 8.1 Hz, 5-H), 6.70 (1H, d, J=2.1 Hz, 3-H), 4.28 (2H, br.s, —NH$_2$), 2.72 (2H, d, J=5.7 Hz, —SCH$_2$), 1.5-1.2 (9H, m), 1.27 (9H, s, t-Bu), 0.87 (3H, t, J=6.6 Hz, —CH$_3$), 0.86 (3H, t, J=6.6 Hz, —CH$_3$)

Exemplified Compound (21) PTS Salt

H-NMR (CDCl$_3$): δ(TMS)=10.5-8.9 (3H br.s, —NH$_3$), 7.76 (1H, d, J=2.1 Hz, 3-H), 7.74 (2H, d, J=7.9 Hz, 2-H for PTS), 7.43 (1H, d, J=8.2 Hz, 5-H), 7.28 (1H, dd, J=2.1, 8.2 Hz, 6-H), 7.06 (2H, d, J=7.9 Hz, 3-H for PTS), 2.71 (2H, d, J=6.0 Hz, —SCH$_2$—), 2.31 (3H, s, CH$_3$—, φ for PTS), 1.18 (9H, s, t-Bu), 0.83 (3H, t, J=6.9 Hz, —CH$_3$), 0.74 (3H, t, J=7.2 Hz, —CH$_3$)

Example 2

(Synthesis of Exemplified Compound (21) from 4-tert-butylchlorobenzene; Ferric Chloride was Used as the Iron Compound)

The compound was synthesized according to the synthetic route shown below.

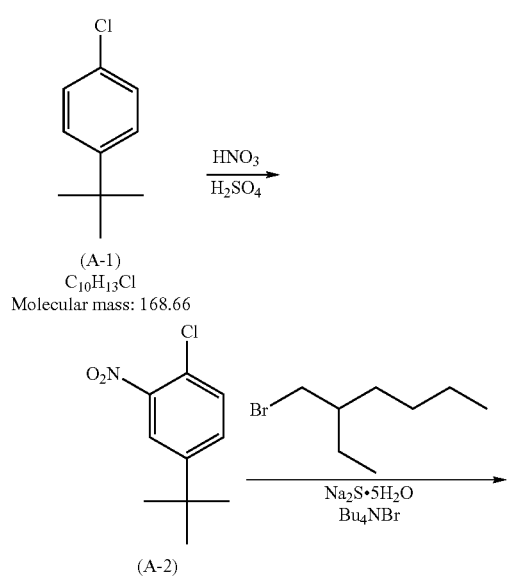

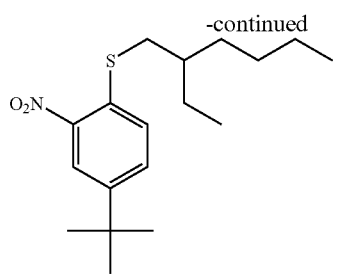

Exemplified compound (1)
C$_{18}$H$_{29}$NO$_2$S
Molecular mass: 323.49

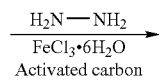

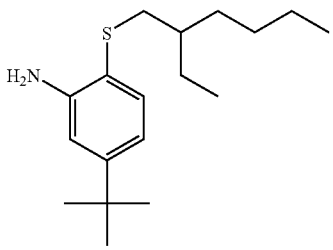

Exemplified compound (21)
C$_{18}$H$_{31}$NS
Molecular mass: 293.51

100 ml of 60% nitric acid was added dropwise to 100 ml of 95% sulfuric acid, at a temperature of 35° C. or less, under ice-cooling, to prepare a mixed acid solution. 100 g (0.593 mol) of 4-tert-butylchlorobenzene (A-1) was added dropwise to this mixed acid solution, at a temperature of 30° C. or less, followed by after-reaction (20 to 25° C.) for 2.5 hours. The reaction solution was poured into cold water, and it was then extracted with 100 ml of toluene, followed by washing with water, to obtain a toluene solution of (A-2).

Meanwhile, a mixture of 299 g (1.779 mol, 3.0 eq) of Na$_2$S.5H$_2$O, 19.1 g (59.3 mmol, 0.1 eq) of tetra-n-butylammonium bromide (BU$_4$NBr), and 360 ml of water, was heated to 70° C., to dissolve the mixture. Then, a solution prepared in advance by adding 120.2 g (0.622 mol, 1.05 eq) of 2-ethylhexyl bromide to the toluene solution of (A-2) and by mixing these components uniformly, was added dropwise to the sodium sulfide aqueous solution at 70 to 75° C. After the addition, the mixture was reacted for one hour. The reaction solution was subjected to phase separation, and the target phase was washed with an alkali, and then with water, and concentrated under reduced pressure, to obtain a reaction condensate (purity: 85%) of Exemplified compound (1).

A mixed solution of the above-mentioned Exemplified compound (1), 10.0 g of activated carbon, 1.0 g of FeCl$_3$.6H$_2$O, and 400 ml of isopropyl alcohol, was heated under refluxing for 10 minutes. Then, 63.1 g of an aqueous 80% hydrazine monohydrate solution was added dropwise to the solution over one hour or more. After the addition was finished, the mixture was reacted under refluxing for 6 hours. The reaction solution was cooled to 40° C. and subjected to filtration using celite, followed by washing with 200 ml of toluene. 500 ml of water was added to the filtrate, to carry out phase separation, and the separated phase was washed with 400 ml of an aqueous 0.45 mass % dilute hydrochloric acid solution, to carry out phase separation. 400 ml of water was further added to the solution and the solution was neutralized by adding aqueous sodium bicarbonate, and phase separation was conducted, to obtain a toluene solution of Exemplified compound (21).

To this solution, 400 ml of toluene was added, and then 112.7 g (59.3 mmol, 1.0 eq) of p-toluenesulfonic acid monohydrate was added, and dissolved under heating. Then, the solution was cooled for crystallization, thereby obtaining 207 g (yield: 75%) of p-toluene sulfonic acid (PTS) salt of Exemplified compound (21).

Example 3

Studies were made as to the effect of the presence of activated carbon and as to a difference in the type of activated carbon, in the same reaction conditions as in Example 2. The results are described collectively in Table 1. The reaction was evaluated by the area value (area %; detection wavelength: 254 nm) in high performance chromatography (HPLC). It can be seen from Table 2 that when no activated carbon was used, the reaction was suspended on the way and the raw material (Exemplified compound (1)) and the hydroxylamine compounds (reduction intermediate; a compound obtained by reducing the nitro group of the exemplified compound (1) to hydroxylamino group) remained in a large amount.

The reaction solution was subjected to phase separation, and the target phase was washed with an alkali, and then with water, and concentrated under reduced pressure, to obtain a reaction condensate (purity: 85%) of Exemplified compound (1).

A mixed solution of 200 g of the thus-obtained reaction condensate of Exemplified compound (1), 10 g of activated carbon, 5.0 g of hydrated iron (III) oxide, and 400 ml of ethanol, was heated under refluxing for 10 minutes. Then, 63.1 g of an aqueous 80% hydrazine monohydrate solution was added dropwise to the solution, over one hour or more. After the addition was finished, the mixture was reacted under refluxing for 6 hours. The reaction solution was cooled to 40° C., and subjected to filtration using celite, followed by washing with 200 ml of toluene. 500 ml of water was added to the filtrate, to carry out phase separation, and the separated phase was washed with 400 ml of an aqueous 0.45 mass % dilute hydrochloric acid solution, to carry out phase separation. 400 ml of water was further added to the solution and the solution was neutralized by adding aqueous sodium bicarbonate, to carry out phase separation, thereby obtaining a toluene solution of Exemplified compound (21).

TABLE 1

| | | | Production rate in reduction reaction (HPLC Area %/254 nm) | | | |
|---|---|---|---|---|---|---|
| Run | Reducing agent (Used amount)[1] | Reaction time (hour) | Exemplified compound (21) | Exemplified compound (1) | Nitroso compound | Hydroxylamine compound |
| 1 | HH-80[2]/FeCl$_3$.6H$_2$O (1.7eq/0.1 mass %) | 3[3] | 17.14 | 41.96 | 1.50 | 26.03 |
| 2 | HH-80/FeCl$_3$.6H$_2$O/Activated carbon[4] (1.7eq/0.1 mass %/5.0 mass %) | 13 | 82.13 | 1.91 | 0.15 | 0.07 |
| 3 | HH-80/FeCl$_3$.6H$_2$O/Activated carbon[5] (1.7eq/0.1 mass %/5.0 mass %) | 6.5 | 82.49 | 1.86 | — | — |

[1]Equivalence (eq) or mass % to Exemplified compound (1).
[2]Aqueous 80% hydrazine-monohydrate solution
[3]No generation of N$_2$ gas was observed about one hour after the initiation of the reaction.
[4]Shirasagi A (trade name) manufactured by Takeda Pharmaceutical Company Limited was used.
[5]Taiko K (trade name) manufactured by Futamura Kagaku Chemical Co., Ltd. was used.

Example 4

(Continuous Synthesis from 4-tert-butylchlorobenzene; Hydrated Iron Oxide was Used as the Iron Compound)

100 ml of 60% nitric acid was added dropwise to 100 ml of 95% sulfuric acid at a temperature of 35° C. or less, under ice-cooling, to prepare a mixed acid solution. 100 g (0.593 mol) of 4-tert-butylchlorobenzene (A-1) was added dropwise to this mixed acid solution, at a temperature of 30° C. or less, followed by after-reaction (20 to 25° C.) for 2.5 hours. The reaction solution was poured into cold water, and it was then extracted with 100 ml of toluene, followed by washing with water, to obtain a toluene solution of (A-2).

Meanwhile, a mixture of 299 g (1.779 mol, 3.0 eq) of Na$_2$S.5H$_2$O, 19.1 g (59.3 mmol, 0.1 eq) of tetra-n-butylammonium bromide (Bu$_4$NBr), and 360 ml of water, was heated to 70° C., to dissolve the mixture. Then, a solution prepared in advance by adding 120.2 g (0.622 mol, 1.05 eq) of 2-ethylhexyl bromide to the toluene solution of (A-2) and by mixing the these components uniformly, was added dropwise to the sodium sulfide aqueous solution at 70 to 75° C. After the addition, the mixture was reacted for one hour.

To this solution, 400 ml of toluene was added, and then 112.7 g (59.3 mmol, 1.0 eq) of p-toluenesulfonic acid monohydrate was added and dissolved under heating. Then, the solution was cooled for crystallization, thereby obtaining 207 g (yield: 75%) of p-toluene sulfonic acid (PTS) salt of Exemplified compound (21).

Example 5

(Effects of Catalyst Activity and Activated Carbon in the Iron-Oxide-Catalyst System)

Studies were made as to a difference in the type of catalyst, as to a solvent, and as to the effect of the presence of activated carbon, in the same reaction conditions as in Example 4. The results are described collectively in Table 2. It can be seen from Table 2 that, in the case where the hydrated iron oxide was used in an amount of 1.0 mass %, the reaction proceeded very slowly when no activated carbon was present, however the rate of reaction was accelerated by adding activated carbon. Also, the reaction could be completed in a short period of time, in the presence of activated carbon, by increasing the amount of the catalyst to 2.5 mass %.

TABLE 2

| Run | Reducing agent (Used amount)[1] | Solvent | Reaction time (hour) | Production rate in reduction reaction (HPLC Area %/254 nm) | | | |
|---|---|---|---|---|---|---|---|
| | | | | Exemplified compound (21) | Exemplified compound (1) | Nitroso compound | Hydroxylamine compound |
| 11 | HH-80[2]/Hydrated iron oxide (1.7eq/1.0 mass %) | IPA | 6 | 9.11 | 60.06 | 9.22 | 10.45 |
| 12 | HH-80/Hydrated iron oxide/Activated carbon[3] (1.7eq/1.0 mass %/5.0 mass %) | IPA | 6 | 58.24 | 22.04 | 0.35 | 2.27 |
| 13 | HH-80/Hydrated iron oxide/Activated carbon[3] (1.7eg/2.5 mass %/5.0 mass %) | IPA | 4.5 | 79.54 | 1.04 | — | 0.20 |
| 14 | HH-80/Iron oxide (1.7eq/1.0 mass %) | IPA | 3 | 0.10 | 91.15 | 0.31 | 0.61 |

[1]Equivalence (eq) or mass % to Exemplified compound (1).
[2]Aqueous 80% hydrazine-monohydrate solution.
[3]Taiko K (trade name) manufactured by Futamura Chemical Co., Ltd. was used.
[4]IPA: Isopropyl alcohol.

Comparative Example 1

(Hydrazine Reduction of Exemplified Compound (1) with Using Pd-c)

To 40 ml of isopropyl alcohol, 20 g of 5-tert-butyl-2-(2-ethylhexylthio)nitrobenzene (Exemplified compound (1)) was dissolved. To this solution was added 0.2 g of 10% Pd/C, and the mixture was heated to 70° C. To this solution was added dropwise 6.31 g (100.8 mmol, 1.7 eq) of an aqueous 80% hydrazine monohydrate over 1 hour or more. After the addition was finished, the solution was subjected to after-reaction under refluxing for 4 hours and cooled to 40° C. The reaction solution was subjected to filtration using celite. When the filtrate was measured by HPLC, the yield of the target Exemplified compound (21) was about 6% in terms of HPLC area %, and the remainder components were mainly the raw material and reduction intermediate (hydroxylamine compound).

In addition to the above examples, studies using various activated Raney nickel were made. However, the reaction was unable to complete, as in the case in the above-mentioned reaction.

Comparative Example 2

(Reduction of the Exemplified Compound (1) by a Reduced Iron)

A reduction reaction was conducted in the same scale as that described in Example 1. An isopropyl alcohol/water solution (20 ml/5 ml) containing 20 g of reduced iron and 1 g of ammonium chloride was heated under refluxing, in advance. To this solution was added, dropwise, a solution obtained by dissolving 20 g of 5-tert-butyl-2-(2-ethylhexylthio)nitrobenzene in isopropyl alcohol (20 ml), over one hour or more. After the addition was finished, the mixture was subjected to after-reaction under refluxing for 1 hour. The reaction solution was cooled to 40° C. and subjected to filtration using celite, followed by washing with 20 ml of toluene. However, filterability when filtering the iron residue was low, bringing about difficult operations. 50 ml of water was added to the filtrate, to carry out phase separation, and the separated phase was washed with 40 ml of an aqueous 0.45 mass % dilute hydrochloric acid solution, to carry out phase separation. 40 ml of water was further added to the solution and the solution was neutralized by adding aqueous sodium bicarbonate, to carry out phase separation, thereby obtaining a toluene solution of Exemplified compound (21). To this solution, 40 ml of toluene was added and then 11.27 g (59.3 mmol, 1.0 eq) of p-toluenesulfonic acid monohydrate was added and dissolved under heating. Then, the solution was cooled for crystallization, thereby obtaining 21.6 g (yield: 75%) of p-toluene sulfonic acid (PTS) salt of Exemplified compound (21).

In this connection, when the amount of the reduced iron to be used was smaller than 20 g, the yield of Exemplified compound (21) was largely dropped.

It is clearly found from the above that in the reduction using reduced iron, although the reduction reaction of nitro group of an aromatic nitro compound having an alkylthio group proceeded, the iron compound was used in a large amount; the filterability of the iron residue remained after the reduction reaction was low, and thus this reduction method was inefficient. From a comparison between Example 1 and Comparative Example 2, the amounts of the reaction agents necessary to reduce 20 g of the aromatic nitro compound were 0.1 g of ferric chloride-hexahydrate and 1.0 g of activated carbon in the method described in Example 1, whereas the amount of the iron powder was as much as 20 g in Comparative Example 2.

It can be seen from the results of Examples and Comparative Examples that the production method of the present invention, characterized by use of a hydrazine compound as a reducing agent, in the presence of an iron compound and an activated carbon, is carried out by a simple operation; the method is reduced in the amount of iron compound to be used, so that generated waste is small; and also, the production process is simplified, which is economically advantageous.

Having described our invention as related to the present embodiments, it is our intention that the invention not be limited by any of the details of the description, unless otherwise specified, but rather be construed broadly within its spirit and scope as set out in the accompanying claims.

What we claim is:

1. A production method of an aromatic amine compound, comprising reducing an aromatic nitro compound which comprises an aromatic ring having, as a substituent, an alkylthio group at an ortho position to a nitro group, to obtain a corresponding aromatic amine compound, wherein the aromatic nitro compound is reduced using a hydrazine compound in the presence of an iron compound and an activated carbon, and wherein the iron compound is present in an amount of from 0.01 to 10.0 mass %, based on the aromatic nitro compound.

2. The production method as claimed in claim 1, wherein the aromatic ring of the aromatic nitro compound further has a tertiary alkyl group as a substituent.

3. The production method as claimed in claim 1, wherein said iron compound is a ferrous or ferric compound.

4. The production method as claimed in claim 3, wherein said iron compound is a ferric compound.

5. The production method as claimed in claim 4, wherein said ferric compound is at least one compound selected from hydrated iron (III) oxide, a ferric halide, a ferric sulfate, and a ferric nitrate.

6. The production method as claimed in claim 1, wherein the aromatic nitro compound is a compound represented by the following formula (II), and the corresponding aromatic amine compound is a compound represented by the following formula (I):

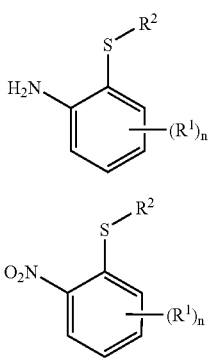

formula (I)

formula (II)

wherein in formulae (I) and (II), $R^1$ represents a substituent; n denotes an integer from 0 to 4; when n is 2 or more, plural $R^1$ s may be the same or different and may combine each other to form a ring; and $R^2$ represents an alkyl group.

7. The production method as claimed in claim 1, wherein the aromatic nitro compound is a compound represented by the following formula (IV), and the corresponding aromatic amine compound is a compound represented by the following formula (III):

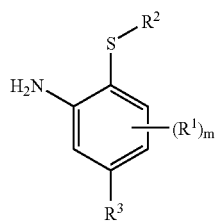

formula (III)

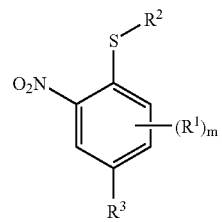

formula (IV)

wherein, in formulae (III) and (IV), $R^1$ represents a substituent, m denotes an integer from 0 to 3; when m is 2 or more, plural $R^1$ s may be the same or different and may combine each other to form a ring; $R^2$ represents an alkyl group; and $R^3$ represents a tertiary alkyl group.

8. The production method as claimed in claim 1, wherein the iron compound is used in an amount of 0.02 to 5.0 mass %, based on the aromatic nitro compound.

9. The production method as claimed in claim 1, wherein the activated carbon is used in an amount of 0.1 to 200 mass %, based on the aromatic nitro compound.

10. The production method as claimed in claim 1, wherein the hydrazine compound is used in an amount of 1.5 to 10.0 mol, per mol of the aromatic nitro compound.

11. The production method as claimed in claim 1, wherein an alkyl moiety in the alkylthio group is a branched alkyl moiety branched at the β-position.

12. The production method as claimed in claim 1, wherein the activated carbon is used in an amount 0.1 to 200 mass %, based on the aromatic nitro compound, and the amount is larger than the amount of the iron compound.

13. A method of producing an aromatic amine compound, comprising:
adding $S^{2-}$ to a system where an aromatic nitro compound having a halogen atom at the ortho position to the nitro group and an alkyl halide coexist, thereby to obtain an aromatic nitro compound having an alkylthio group at the ortho position to the nitro group, and
reducing the aromatic nitro compound using a hydrazine compound, in the presence of an iron compound and an activated carbon to give a corresponding aromatic amine compound.

14. The production method as claimed in claim 13, wherein the iron compound is used in an amount of 0.01 to 10.0 mass %, based on the aromatic nitro compound.

15. A method of producing an aromatic amine compound, comprising:
heating a mixture containing an aromatic nitro compound having an alkylthio group at the ortho position to the nitro group, an iron compound, an activated carbon, and a reaction solvent, to a reaction temperature, and
adding a hydrazine compound, thereby to reduce the aromatic nitro compound to give a corresponding aromatic amine compound,
wherein the iron compound is used in an amount 0.01 to 10.0 mass %, based on the aromatic nitro compound.

16. The production method as claimed in claim 15, wherein the hydrazine compound is added dropwise.

* * * * *